US00PP26211P3

(12) United States Plant Patent
Orton

(10) Patent No.: US PP26,211 P3
(45) Date of Patent: Dec. 15, 2015

(54) INTERSPECIFIC CORNUS HYBRID TREE DESIGNATED 'KN144-2'

(50) Latin Name: ***Cornus kousa*×*C. nuttallii***
Varietal Denomination: KN144-2

(71) Applicant: Rutgers, The State University, New Brunswick, NJ (US)

(72) Inventor: Elwin R. Orton, Hillsborough, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 347 days.

(21) Appl. No.: 13/815,598

(22) Filed: Mar. 12, 2013

(65) Prior Publication Data

US 2014/0283242 P1 Sep. 18, 2014

(51) Int. Cl.
*A01H 5/00* (2006.01)
*A01H 5/02* (2006.01)

(52) U.S. Cl.
USPC ..... Plt./220
CPC ..... *A01H 5/02* (2013.01)

(58) Field of Classification Search
USPC ..... Plt./220
CPC ..... A01H 5/00
See application file for complete search history.

*Primary Examiner* — Kent L Bell
(74) *Attorney, Agent, or Firm* — James A. Lucas; Driggs, Hogg, Daugherty & Del Zoppo Co., LPA

(57) ABSTRACT

The physical manner in which the inflorescences on our new cultivar are displayed is unique as the flower heads are held erect on the rapidly elongating peduncles in the spring at nearly 90 degrees. When the telescoped vegetative bracts that protected the over-wintering flower buds have fallen, the rapidly growing peduncles elongate upward and the rapidly growing narrow pink-red floral bracts which are lightly attached at their apex enlarge upward until, with further growth, the floral bracts expand at an increased angle and look like butterflies perched on the vertical peduncles. The deep-cup shape of the floral bracts is unique among the comparative pink/red bracted clones of *C. kousa* 'Rosea', 'Radiant Rose', and 'Heart Throb' in the trade It's floral bracts are larger and darker than the *C. kousa* in the trade and holds its color longer than those of *C. kousa* which usually turn white. This hybrid 'KN144-2' is a winter hardy, attractive dark/pink red floral bracted tree with a beautiful round densely-branched growth habit than other *C. kousa* cultivars. It is more vigorous, dense, more rounded and fully branched, and is slightly taller than wide as compared to those presently in the trade. The bracts of this new cultivar are believed by the inventor to be larger and darker pink/red than those of any of the other pink/red cutivars of *C. kousa.*

5 Drawing Sheets

Latin name of genus and species of the plant claimed: *Cornus kousa*×*C. nuttallii.*

Variety denomination: 'KN144-2'.

CROSS REFERENCE TO RELATED APLICATIONS

NONE

STATEMENT REGARDING FEDERALLY SPONSORED RESEARCH OR DEVELOPMENT

NONE

BACKGROUND OF THE INVENTION

This invention is the product of a long continuing program of interspecific hybridization of dogwood trees for introduction to commerce. One of the objects of this program was to develop a dark pink-red bracted *Cornus kousa* habit or tree form exhibiting floral bract color that is superior to that of plants in the trade known as 'Rosea', 'Radiant Rose', and 'Heart Throb'. This research resulted in the production of a pink bracted cutivar 'KN144-2' of *C. kousa* size and habit. 'KN144-2' has been found to maintain more intense pink-red pigmentation of the floral bracts for a greater length of time especially during extended hot weather of three weeks or more than those currently in the trade.

A very vigorous F1 interspecific hybrid seedling among the progeny from a successful cross (Apr. 20-21, 1973) of *Cornus kousa*×*C. nuttallii* 'Goldspot' was used as the seed parent (KN3-3) in a species-backcross with *C. kousa* 'Rosea'. Then a healthy, white-bracted seedling (KN30-4) was crossed with an unnamed plant of *C. kousa* to obtain progeny of the second species-backcross. Again, a typical white-bracted seedling (KN109-92) was used to obtain progeny from a third species-backcross wherein 'Rosabella' was used as the pollen parent. From this third serial species-backcross, a superior seedling 'KN144-2' was selected. These aforementioned crosses are shown in the pedigree chart below. None of the antecedent parent plants are patented.

| | | Progeny number |
|---|---|---|
| Initial Fl cross | K23 *C. kousa* x. D88 *C nuttallii* 'Goldspot' = | KN3 |
| Backcross 1 | KN3-3* x *C. kousa* 'Rosea' = | KN30 |
| Backcross 2 | KN30-4* x unnamed *C. kousa* seedling = | KN109 |
| Backcross 3 | KN109-92* x *C. kousa* 'Rosabella' = | KN144 |
| New Cultivar | 'KN144-2' | |

*Seedling number

The particular seedling, 'KN144-2' was selected from the progeny of the third backcross generation grown in a cultivated area and, as a result, have in turn caused the same to be asexually reproduced by grafting, (usually by T-budding or chip-budding). It also can be propagated by softwood stem cuttings. The reproduction and actual growth and selection of the new cultivar took place in the vicinity of New Brunswick, N.J. and has been found to be distinctive as to its winter-hardiness in that area, USDA Plant Hardiness Map Zone 6a.

As will be understood from the detailed description of the invention which appears hereinafter, the new cultivar is in fact outstanding and readily identified as being such. With the foregoing in mind, the description that follows will be understood as clearly defining the new cultivar, the desirable characteristics of which are the result of such a program as has been heretofore described.

SUMMARY OF THE INVENTION

The germinated seedling, which became the new cultivar 'KN144-2', was transplanted from its seedling flat in the greenhouse to a one-gallon container on Dec. 18, 1996 and subsequently transplanted to the position of Row 11, Plant 13 in Research Field #70 at a turf research farm of a New Jersey state university at Adelphia, N.J. in October 1997. After the performance of this plant had been evaluated in this field for six growing seasons, it became clear that this plant exhibited superior characteristics in growth habit and ornamental display including excellent branching, leaf characteristics, and dark pink/red floral bracts and excellent fall foliage color, plus drought tolerance, winter hardiness, and freedom from dogwood pests or diseases. In October 2003 this plant was transplanted to a smaller research field at Millstone, N.J. where it is now growing as a 16-year-old plant. Also, it has been propagated by nurserymen in Tennessee and Oregon under a formal testing agreement with said New Jersey state university.

BRIEF DESCRIPTION OF THE DRAWINGS

This new variety of dogwood is illustrated by the accompanying photographic drawings, depicting the plant by the best possible color representation using color photography. All color references below are measured against The Royal Horticultural Society Colour Chart (R.H.S. 1966 Ed.). Colors of foliage, floral bracts, and other plant parts may vary from year to year depending on horticultural practices, light conditions, air temperature, soil fertility, etc.

BOTANICAL DESCRIPTION OF THE INVENTION

PLANT

Figure 1:
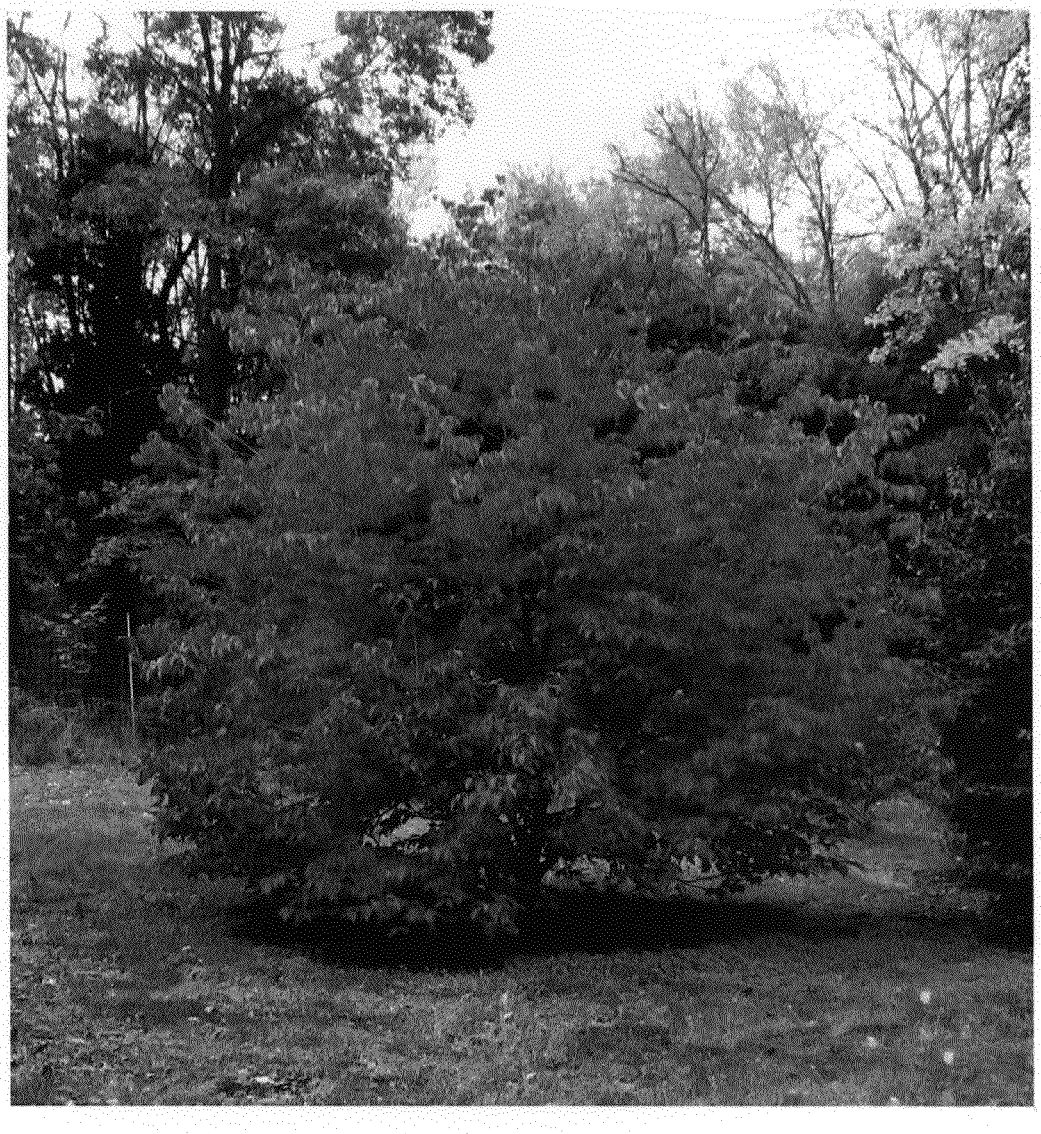
FIG. 1 shows fall color and shape of original seedling tree of the present invention.
Figure 2:
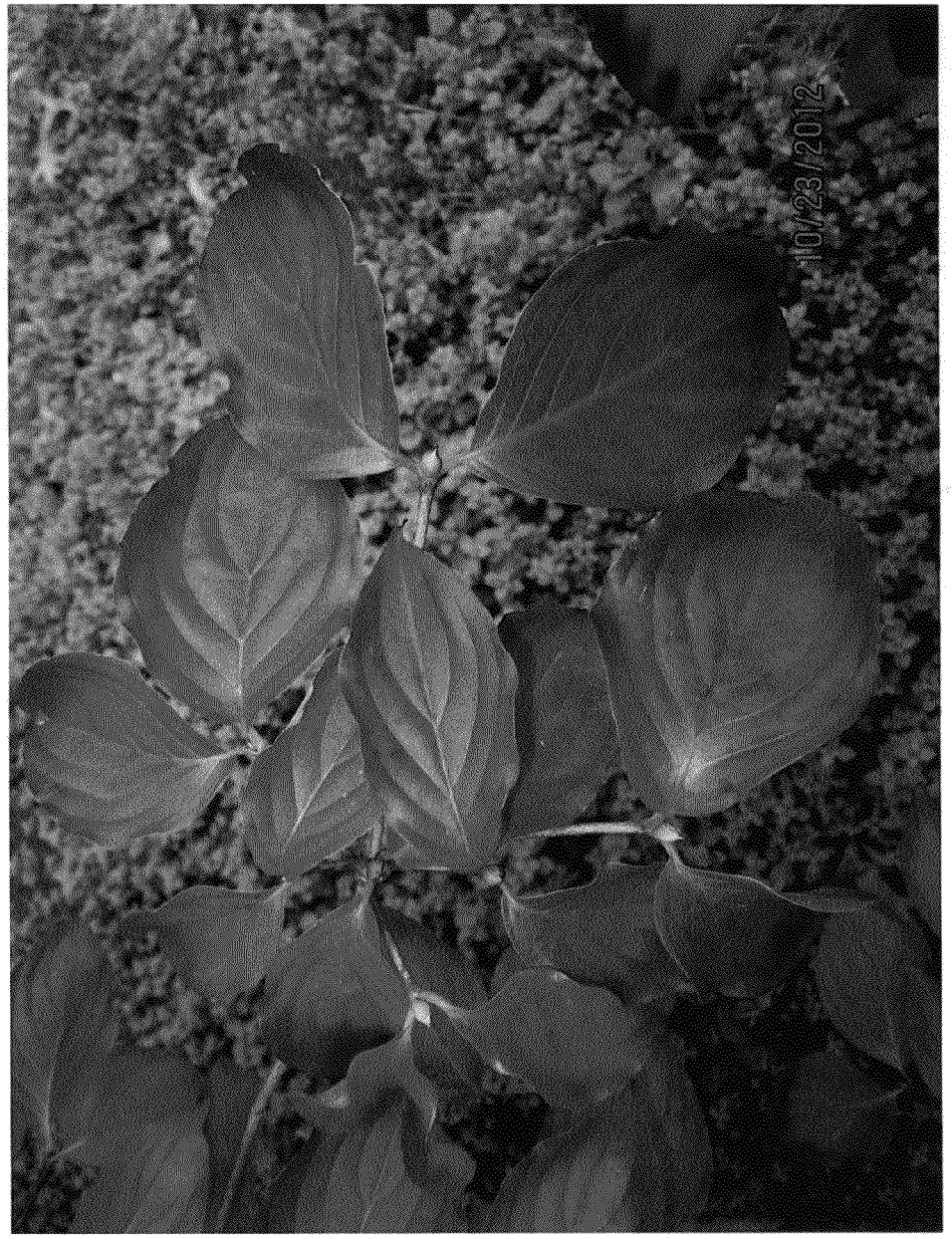
FIG. 2 shows winter buds and fall color of foliage.
Figure 3:
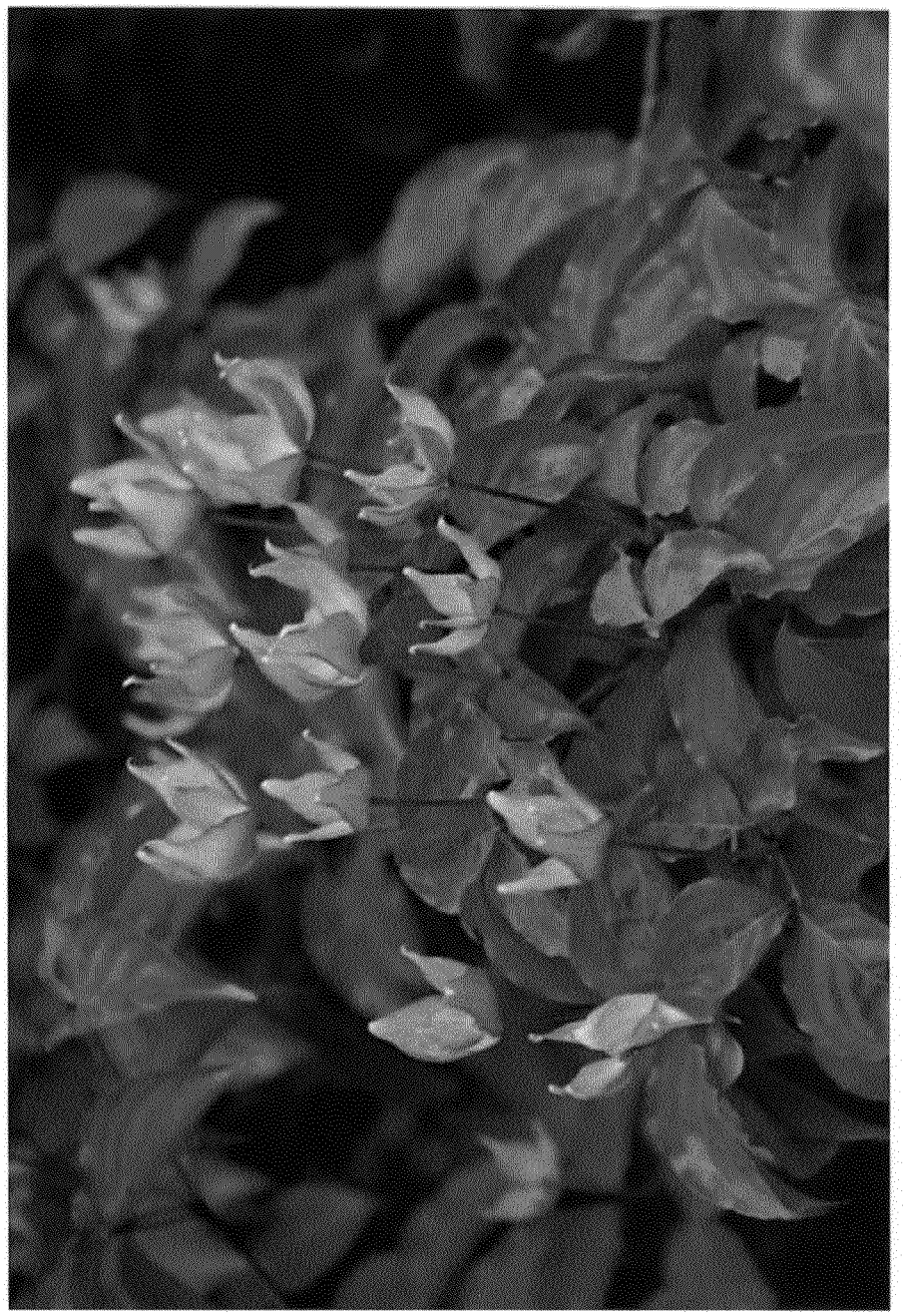
FIG. 3 shows floral bracts—signature cup-shaped.
Figure 4:
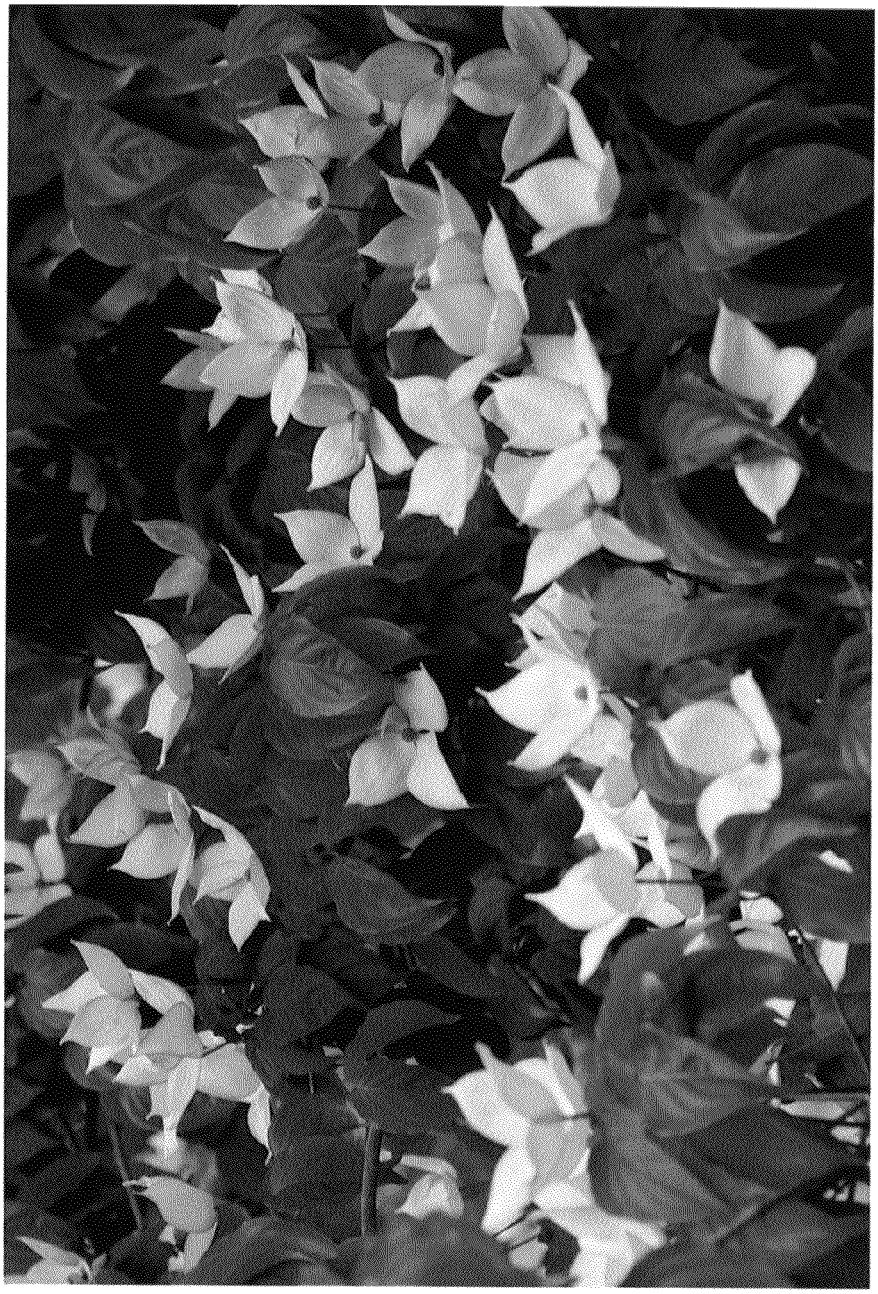
FIG. 4 shows floral bracts—one week later.
Figure 5:
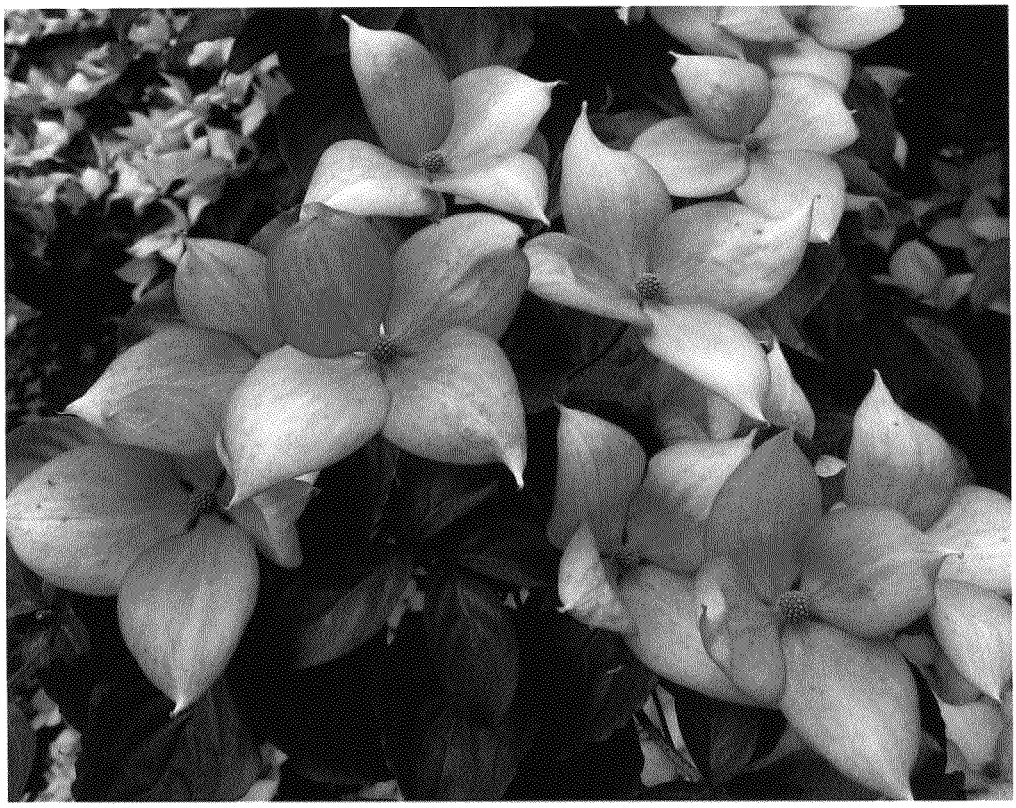
FIG. 5 shows close-up of cup-shaped floral bracts.

Form: Tree.

Growth habit: Densely branched low to ground and forms a rounded head slightly wider than tall.

*Height.*—5.2 meters at 16 years.

*Spread.*—5.8 meters at 16 years.

Plant vigor: Moderate vigor typical of most seedlings of the rubra variety of *C. kousa* currently in the trade, such as 'Satomi' (unpatented), 'Rosabella', 'Schmred' (patented) 'Rosea', 'Benifuji' (patented) and 'Hanros' (aka 'Radiant Rose', (also patented)).

Cold hardiness: Original seedling has suffered no winter injury during the 16 years it has been observed in the field in the vicinity of New Brunswick, N.J. in USDA Plant Hardiness Map Zone 6a (−20° to −23° C.).

Trunk: Circumference of the crown of the original seedling at the soil level was 48.3 cm after 16 growing seasons with heavily exfoliating bark on the trunk and base of large branches up to 48.3 cm high. Moderately exfoliating bark on the upper trunk.

*Color.*—Under exfoliating bark close to 199D Greyed-Brown Group, outer exfoliating bark black gray with lenticels.

*Texture.*—Sandpaper rough, bark exfoliating at basal 1.52 m of trunk area.

*Lenticels.*—Numerous but too indistinct to count.

Branches: Six trunks with five low branches coming off the trunk at 35°-45° angles. Main branches starting at 28 cm above soil level. Young branches quite smooth except for presence of lenticels.

*Color.*—Closest to 197A Grey-Green Group.

*Crotch angle.*—35°-45° angles.

*Lenticels.*—Present on younger and smaller branches but not sufficiently distinct to provide any measure of number or density.

*Texture.*—Smooth with a few lenticels.

FOLIAGE

Leaf arrangement: Opposite.

Leaf size: Lamina.

*Length.*—Average 9.99 cm (n=40) (range 7.3-11.8 cm).

*Width.*—Average 6.67 cm (n=40) (range 4.6-9.5 cm). (n=number of observations).

*Shape.*—Ovate.

*Apex.*—Cuspidate.

*Base.*—Broadly attenuate.

*Margin.*—Mildly crenulate.

Texture: Adaxial leaf surface is smooth. Abaxial leaf surface coarse due to prominently ridged midrib and lateral veins.

Other features: Lamina flat with many short, fine, white hairs. Prominent brown tufts clustered in the axil of each vein and midrib in the uppermost 2, sometimes 3, opposing sets of veins. Also a few hairs scattered along the midrib.

Quantity: Moderately dense.

Coloration: Solid.

Mature foliage color: Adaxial: Closest to 144A Green Group with veins 187C Greyed-Purple group and in tip and margins.

*Abaxial.*—Closest to 146D Yellow-Green Group. Autumn foliage color at Millstone, N.J.

*Adaxial surface.*—167A Grey-Orange Group.

*Abaxial surface.*—181A Grey-Red Group. Leaf color is clearly dependent on many environmental factors such as soil type, exposure to sun, air temperature, day length, available water and nutrients. Thus, leaf color may vary from one area to another.

INFLORESCENCE

Location where observations were made: Research field in Millstone, N.J.

Type of inflorescence: Flower head is a dense, basically rounded mound but slightly more narrow at top.

Over-wintering flower buds: 7.7 mm high and 5.5 mm wide. (n=12).

Peduncle: In winter months, about 2 mm long and 2 mm wide. Is completely covered, or enclosed, by 3 sets of opposing appressed bracts. These valvate bracts are telescoped on the peduncle immediately below its point of attachment to the receptacle of the rounded flower head. These vegetative bracts are uniformly wide at the point where they surround the flower head but about that point they taper to a blunt apex over the flower head close in slightly and taper to a blunt apex over the flower head. Their color is 183A Greyed-Purple Group.

Peduncle length in May: The peduncle has grown rapidly from its 2 mm size in winter to become 7 cm tall and the inflorescence is ready to display the true flowers. One side was 144B Yellow-Green Group and side two 51A Red Group with tip and base end green and stippled reddish-pink center on green stalk.

Peduncle size at time of flowering:

| Year | no. | Length cm Average | Width mm Average |
|---|---|---|---|
| 2005 | 13 | 8.58 | 1.42 |
| 2008 | 15 | 7.36 | 2.10 |
| 2009 | 25 | 6.72 | 1.86 |
| 2012 | 5 | 7.72 | 1.96 |

FLORAL BRACTS

Number: Four, in two opposing pairs.

Size of floral bracts: Average Length and Width of Floral Bracts (in centimeters)

| | | Inner bracts | | Outer bracts | | | Outer |
|---|---|---|---|---|---|---|---|
| Year | No. of Bracts | Length cm | Width cm | Length cm | Width cm | Inner Involucral | Spread cm |
| 2008 | 20 | 6.9 | 5.1 | 7.0 | 5.3 | 14.1 | 14.3 |
| 2011 | 40 | 6.4 | 4.6 | 6.6 | 4.5 | 13.1 | 13.6 |

The size of the floral bracts on plants of 'KN144-2' varies from year to year due to the many environmental factors influencing the annual growth of trees. However, the floral bracts of our new hybrid are larger than those of any of the pink/red bracted cultivars of *C. kousa* previously mentioned heretofore. The inner and outer bracts, including involucral spread, are similar in size and shape.

Color: Start of floral display (early to mid-May).

*Adaxial surface.*—51A Red Group — deeper color around edges, tip and basal end is 2D Yellow Group.

*Abaxial surface.*—2D Yellow Group with pink veins and thin pink line at margin. Very thin parallel lines and extreme pronounced veins on abaxial and adaxial surface.

Shape: Ovate, with slightly overlap of the basal 30% of the length of neighboring bracts.

Apex: Apiculate.

Base: Obtuse with winged stalk, 4-5 mm wide at point of attachment to peduncle and 5-10 mm long.

Bract stalk length and width: Insignificant.

Flower description: Very floriferous. Single flowers arranged in compact, dense heads subtended by the large floral bracts. No observed fragrance. Flowers not persistent. Floral display typically lasts about three weeks or more, depending on weather conditions.

Flowering habit: Anthesis of the tiny, relatively inconspicuous true flowers generally commences 5-6 days following the onset of the ornamental display of the large floral bracts which generally occurs in central New Jersey in mid-May and continues approximately for 2.5 to 3 weeks or more depending on the prevailing weather conditions. Floral development is asynchronous within the inflorescence. The average number of true flowers per flower head of this new cultivar is quite uniform from year to year. Number of true flowers per flower head: average of 44.2 with a range of 37-57 flowers per head (n=30 flowers). True flowers are tiny and relatively inconspicuous (each with four minute sepals, petals and stamens, and one pistil.)

REPRODUCTIVE ORGANS

Stamens: Number per flower — 4. All parts of each organ are minute in size and are insignificant.

FRUIT

Flower head with mature fruit: Fruits are 2-celled, typically 1 seeded, fleshy drupes that form a mounded raspberry-liksyncarp averaging 2.39 cm in height and 2.84 cm. in width with a flat base (averages based on 50 measurements each). The many ovaries are enclosed in a fleshy rounded mass typical for fruit of *C. kousa*. The exterior of the aggregate fruit is fairly smooth except for the dried floral parts at the tip of each individual drupe: i.e. the dried remains of the sepals and the persistent style and stigma. Color varying at green to yellow to orange to pink as the fruit starts out as 46A Red Group and matures in color to 42C Red Group. Fruit ripen in late August and persist for six weeks or more unless eaten by birds or animals.

Seed:

*Color.*—Closest to 199D Grey-Brown Group.

*Size.*—Averaging 5.72 mm (range 4.50-7.00 mm) length; 4.39 mm (range 3.25-6.20 mm) width; and 2.8 mm (2.00-3.50 mm) in thickness.(n=20).

*Shape.*—Typical for *C. kousa.*

Resistance to insects and diseases: No insect or disease problems were observed during the 15 years the original seedling of the variety 'KN144-2' has been tested in the field.

What is claimed is:

1. A new and distinct cultivar of dogwood tree, substantially as herein shown and described, comprising an advanced generation interspecific hybrid of (*Cornus kousa*×*C. nuttallii*) with various *C. kousa.*

* * * * *